United States Patent
Han (10) Patent No.: US 9,761,806 B1
(45) Date of Patent: Sep. 12, 2017

(54) SENSORS WITH INTEGRATED DATA PROCESSING CIRCUITRY

(71) Applicant: International Business Machines Corporation, Armonk, NY (US)

(72) Inventor: Shu-jen Han, Cortlandt Manor, NY (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 0 days.

(21) Appl. No.: 15/274,058

(22) Filed: Sep. 23, 2016

(51) Int. Cl.
- G06N 99/00 (2010.01)
- H01L 51/00 (2006.01)
- H01L 51/05 (2006.01)

(52) U.S. Cl.
CPC ....... *H01L 51/0048* (2013.01); *G06N 99/005* (2013.01); *H01L 51/0003* (2013.01); *H01L 51/0094* (2013.01); *H01L 51/0558* (2013.01)

(58) Field of Classification Search
None
See application file for complete search history.

(56) References Cited

U.S. PATENT DOCUMENTS

| 8,272,280 | B2 | 9/2012 | Jones, Jr. | |
|---|---|---|---|---|
| 2002/0171079 | A1* | 11/2002 | Braun | B82Y 10/00 257/40 |
| 2004/0150010 | A1* | 8/2004 | Snider | B82Y 10/00 257/209 |
| 2005/0015351 | A1* | 1/2005 | Nugent | G06N 3/063 706/33 |
| 2007/0134866 | A1 | 6/2007 | Huang et al. | |
| 2009/0326833 | A1* | 12/2009 | Ryhanen | G06N 3/0675 702/33 |
| 2011/0176359 | A1* | 7/2011 | Bertin | G06N 3/063 365/167 |
| 2012/0150780 | A1* | 6/2012 | Nugent | G06N 3/063 706/33 |
| 2012/0326126 | A1 | 12/2012 | Chen et al. | |
| 2013/0168794 | A1 | 7/2013 | Fu et al. | |
| 2013/0209991 | A1 | 8/2013 | Wang et al. | |

(Continued)

FOREIGN PATENT DOCUMENTS

KR  1020160017684 A  2/2016

OTHER PUBLICATIONS

Cao et al, Ultrathin Films of Single-Walled Carbon Nanotubes for Electronics and Sensors: A Review of Fundamental and Applied Aspects, 2009.*

(Continued)

*Primary Examiner* — Stanley K Hill
*Assistant Examiner* — Mikayla Chubb
(74) *Attorney, Agent, or Firm* — Cantor Colburn LLP; Vazken Alexanian (57) ABSTRACT

A system for sensing data includes one or more sensors formed on a substrate, including flexible substrates. A plurality of transistors are coupled to the one or more sensors and formed on the substrate. Each transistor of the plurality of transistors is constructed with a channel formed of a nanoscale material. The plurality of transistors are configured to perform computing tasks such that data processing and classification are performed directly on the sensor substrate. The nanoscale material can include carbon nanotubes.

15 Claims, 4 Drawing Sheets

(56) References Cited

U.S. PATENT DOCUMENTS

| | | | |
|---|---|---|---|
| 2014/0070169 A1* | 3/2014 | Zhou | H01L 27/3274 257/29 |
| 2015/0104783 A1 | 4/2015 | Al Ahmad | |
| 2015/0236283 A1* | 8/2015 | Afzali-Ardakani | G06N 3/063 365/182 |
| 2016/0129455 A1 | 5/2016 | Wang et al. | |
| 2016/0139019 A1 | 5/2016 | Avouris et al. | |
| 2016/0144358 A1 | 5/2016 | Patel | |
| 2016/0180019 A1* | 6/2016 | Van Rooyen | G06F 19/24 702/19 |
| 2016/0190494 A1* | 6/2016 | Xiao | H01L 51/0554 257/29 |
| 2017/0005281 A1* | 1/2017 | Afzali-Ardakani | G06N 3/063 |

OTHER PUBLICATIONS

Maune et al, Self-assembly of Carbon Nanotubes into Two-dimensionsal Geometries using DNA Origami Templates, 2010.*

Qian et al, Neural network computation with DNA strand displacement cascades, 2013.*

D. Lee et al., "Logic circuits composed of flexible carbon nanotube thin-film transistor and ultra-thin polymer gate dielectric", Scientific Reports 6: 26121, 2016, pp. 1-7.

J. Lobez et al., "Surface Selective One-Step Fabrication of Carbon Nanotube Thin Films with High Density", ACS Nano, vol. 8, No. 5, 2014, pp. 4954-4960.

Q. Cao et al., "Arrays of single-walled carbon nanotubes with full surface coverage for high-performance electronics", Nature Nanotechnology, 8, 2013, pp. 180-186.

T. Moy et al.,"A Flexible EEG Acquisition and Biomarker Extraction System Based on Thin-Film Electronics," IEEE Int'l Solid-State Circuits Conf. (ISSCC), Feb. 2016, pp. 294-295.

W. Rieutort-Louis et al., "A Large-Area Image Sensing and Detection System Based on Embedded Thin-Film Classifiers," IEEE J. Solid-State Circuits (JSSC), vol. 51, No. 1, Jan. 2016, pp. 281-290.

Z. Hu et al., "Physically unclonable cryptographic primitives using self-assembled carbon nanotubes", Nature Nanotechnology, 11, 2016, pp. 559-565.

* cited by examiner

SENSORS WITH INTEGRATED DATA PROCESSING CIRCUITRY

BACKGROUND

The present invention relates in general to integrated circuit device structures and their fabrication. More specifically, the present invention relates to the fabrication of sensors with integrated data processing circuitry in the form of transistors using nanoscale technology.

Sensors are used to monitor people, places and objects. There are many different types of sensors, including, for example, wearable sensors that keep track of the health of the wearer (e.g., a heart rate monitor or an electrocardiogram (ECG) sensor). Sensors can also be used to keep track of environmental conditions such as temperature, humidity, moisture, pressure, wind, and the like.

SUMMARY

Embodiments herein are directed to a system for sensing data. The system includes one or more sensors formed on a substrate. A plurality of transistors are coupled to the one or more sensors and formed on the same substrate. Each transistor of the plurality of transistors includes nanoscale materials.

Embodiments described herein are also directed to a method of sensing data. The method includes sensing data using one or more sensors formed on a substrate. A plurality of transistors coupled to the one or more sensors and formed on the substrate is used to performing computing tasks on the data. Each transistor of the plurality of transistors includes nanoscale materials.

Embodiments described herein are also directed to a computer-readable storage medium having program instructions embodied therewith. The computer-readable storage medium is not a transitory signal per se, the program instructions readable by a processor system to cause the processor system to perform a method. The method includes performing analog-to-digital conversion of data from one or more sensors. The method further includes performing feature extraction of data from the one or more sensors, wherein feature extraction includes processing data to determine important characteristics of the data. The method further includes perform computing tasks including classifying data from the one or more sensors. Classifying data from the one or more sensors includes using machine-learning techniques to classify data. Classifying data further includes using historical data from the sensor to improve the machine-learning techniques. The processor system includes a plurality of transistors formed on a on a substrate. The processor system is coupled to one or more sensors that are formed on the substrate. A channel of each transistor of the plurality of transistors includes a nanoscale material.

Additional features are realized through the techniques of the present invention. Other embodiments are described in detail herein and are considered a part of the claimed invention. For a better understanding of the invention with the features, refer to the description and to the drawings.

BRIEF DESCRIPTION OF THE DRAWINGS

The subject matter which is regarded as the invention is particularly pointed out and distinctly claimed in the claims at the conclusion of the specification. The forgoing features are apparent from the following detailed description taken in conjunction with the accompanying drawings in which:

DETAILED DESCRIPTION

It is understood in advance that although a detailed description of an exemplary sensor system is provided, implementation of the teachings recited herein are not limited to the particular structure described herein. Rather, embodiments of the present invention are capable of being implemented in conjunction with any other type of transistor, now known or later developed.

For the sake of brevity, conventional techniques related to semiconductor device and integrated circuit (IC) fabrication may or may not be described in detail herein. Moreover, the various tasks and process steps described herein can be incorporated into a more comprehensive procedure or process having additional steps or functionality not described in detail herein. In particular, various steps in the manufacture of semiconductor devices and semiconductor-based ICs are well-known and so, in the interest of brevity, many conventional steps will only be mentioned briefly herein or will be omitted entirely without providing the well-known process details.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

As used herein, the terms "invention" or "present invention" are non-limiting terms and not intended to refer to any single aspect of the particular invention but encompass all possible aspects as described in the specification and the claims.

One characteristic of some types of sensors is the need to transmit data. Typically, a sensor does not process data. A sensor merely senses data, then sends the data to a different location for processing, using various types of transmission technology. As described above, many traditional sensors are used to sense analog waveforms (such as weather conditions, speed, strain, body conditions, sound levels, light levels, equipment conditions, and the like). In many cases, the goal of such a sensor is to gather analog data as completely as possible and transmit the analog data for processing by a second device. In the second device, a high-quality analog to digital converter is used to convert the analog data to a digital format for processing. For some sensors, that might not be a problem, as the data is processed in close proximity and there are few sensors. For example, a "smart watch" might have a single heart rate sensor and a processor right next to it.

As sensors become more prevalent (for example, the "Internet of Things" can have allow multiple sensors that are coupled to transceivers with Internet connectivity), the data can become processed at a more distant location. The need to transmit the data can be more problematic in those cases. Because sensors are becoming more plentiful, more data from more sensors are being transmitted for centralized processing. A person, vehicle, device, or a building might have many sensors, each of which is capturing a large amount of analog data. The data stream from each sensor will have to be transmitted before being processed. This approach will lead to a limit on the ability to provide timely feedback for decision-making or to control a feedback loops. In addition, there can be energy, computational, or communication abilities that can be compromised by the transmission of too much data.

It is desirable to be able to process sensor data on the same substrate as the sensor in order to perform real-time analytics. This can be difficult to accomplish today due to the lack of versatile technology that can be easily fabricated on various substrates, such as flexible and large-area substrates that sensors can be constructed upon.

To illustrate with an exemplary situation, a heart rate monitor senses many pieces of data, including the data from each beat of the heart. But the data can also include data between each heartbeat. While such data can be important in some uses (such as an ECG, for example), it might not be important for a heart rate monitor that is only concerned with the rate at which the heart is beating. If the raw data is computed remotely, the entire data stream or waveform from the heart rate monitor must be transmitted to the processor. This problem is exacerbated for each sensor in a system. As the "Internet of Things" becomes more prevalent, the number of sensors is quickly growing, resulting in a great deal of information that must be transmitted and processed. However, if the raw data is computed locally (at or near the sensor), only a single number (the instantaneous heart rate) needs to be transmitted, and it can be transmitted at a lower rate (e.g., once per second), thereby using less power. While the above description specifically references heart rate sensors, it should be understood that the concepts described herein are applicable to any type of sensor.

Turning now to an overview of the present invention, one or more embodiments bring the computation power to process data from the sensors directly to the front-end, right next to (or directly integrated with) sensors on flexible sensor substrates. These can be used for embedded feature extraction and data compression. In one or more embodiments, such a process uses carbon nanotube ("CNT") technology as the channel material for the transistors of the integrated circuits that are used to process data. The integrated circuits perform data processing, compression, and classification directly on the flexible substrate. In one or more embodiments, machine learning techniques are incorporated to minimize design variation of the sensors and the CNT transistors, and to perform feedback on the sensed data.

The use of flexible materials as the substrate of a transistor and sensor means that traditional channel materials cannot be used. This has resulted in several different types of materials proposed as the channel material. These can include polysilicon, amorphous silicon, organic channel materials, and oxides (such as zinc oxide). Each of those channel materials has drawbacks. For example, polysilicon requires a high process temperature (above 400 degrees Celsius), which makes it difficult to use with most flexible substrates. Amorphous silicon, organic channel materials, and oxides (such as zinc oxide) do not have the high process temperature problem. However, they are each limited to a single type of transistor (n-type for amorphous silicon and zinc oxide, p-type for organic channel materials). In addition, amorphous silicon, organic channel materials, and zinc oxide each have a low mobility. It is desirable to have a channel material for use in technologies with flexible substrates including, but not limited to, thin film transistors.

As noted above, embodiments of the present invention use carbon nanotube or other nanoscale technology as the channel material of transistors. In comparison to other technologies for channel, carbon nanotube technology satisfies all requirements for in-sensor computing on large-area flexible substrates. A higher mobility means faster transistor speed, or lower power consumption for the same transistor speed. The process temperature for the carbon nanotube channel is relatively low, 150 degrees Celsius. CNT technology allows both n-type and p-type transistors to be formed. And the cost is very low compared to the channel materials discussed above.

The use of carbon nanotube channels allows sensors to include information processing technology in the form of transistors at or near the location of the sensor (such as in the same package). This allows all necessary circuit functions for data processing, compression, and classification to be built directly on the flexible sensor substrate.

Turning now to a more detailed description of an embodiment of the present invention, an exemplary transistor on a flexible substrate will now be described with reference to FIGS. 1 through 4. It should be noted that, although some of the examples specifically refer to flexible substrates, embodiments of the present invention are also operable on non-flexible substrates.

Figure 1:
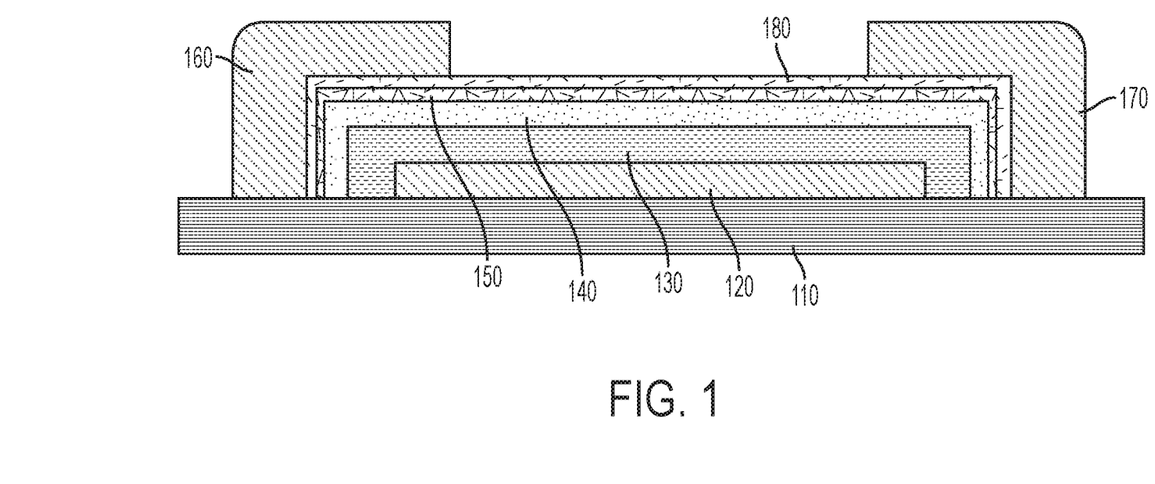
FIG. 1 depicts a side view of an exemplary transistor structure on a flexible substrate according to one or more embodiments.

Referring now to FIG. 1, an exemplary transistor 100 is presented. It should be understood that transistor 100 is merely exemplary and other embodiments can use other transistor structures. Transistor 100 includes flexible substrate 110. Flexible substrate 110 can be constructed from one of a variety of different materials. Exemplary flexible substrates include, but are not limited to polydimethylsiloxane (PDMS), polyimide (PI), polyurethane (PU), polymethylmethacrylate (PMMA), polyethylene terephthalate (PET), polystyrene, polycarbonate, polyvinyl alcohol (PVA), polybenzimidazole, polyester. Atop flexible substrate 110 is a gate metal 120. In some embodiments, silver is used as the gate metal. In some embodiments, copper is used as the gate metal. In some embodiments, gold is used as the gate metal. Other metals can be used.

In some embodiments, there is another gate metal 130 above gate metal 120. In some embodiments, gate metal 130 is titanium, though other materials can be used, including, but not limited to, gold, aluminum, and palladium. Above the gate metal is a gate dielectric 140. In some embodiments, gate dielectric 140 can be constructed from an aluminum oxide such as $Al_2O_3$. Other dielectric materials also can be used. There can be a layer 150 atop the gate dielectric that helps the deposition of the channel material. In some embodiments, layer 150 is a 3-Aminopropyl triethoxysilane (APTES) material, which is an aminosilane used for silanization. A source 160 and drain 170 are above the above-described structure, surrounding it. Source 160 and drain 170 can be constructed of one of a variety of different materials, including, but not limited to, palladium, nickel, gold, and chromium. Source 160 and drain 170 are coupled to, and on opposing sides of, channel 180. Channel 180 is a nanoscale material.

In some embodiments, channel 180 is an allotrope of carbon with a cylindrical nanostructure. Various types of constructions can be used for the carbon nanotube channel. For example, depositing carbon nanotubes from solutions using various surface functionalization techniques can be employed here. In some embodiments, channel 180 can be another nanoscale material, such as a graphene or other 2-dimensional materials such as transition metal dichalcogenide materials, phosphorene etc. The construction of the transistor can occur in one of a variety of techniques now known in the art or developed in the future.

Figure 2:
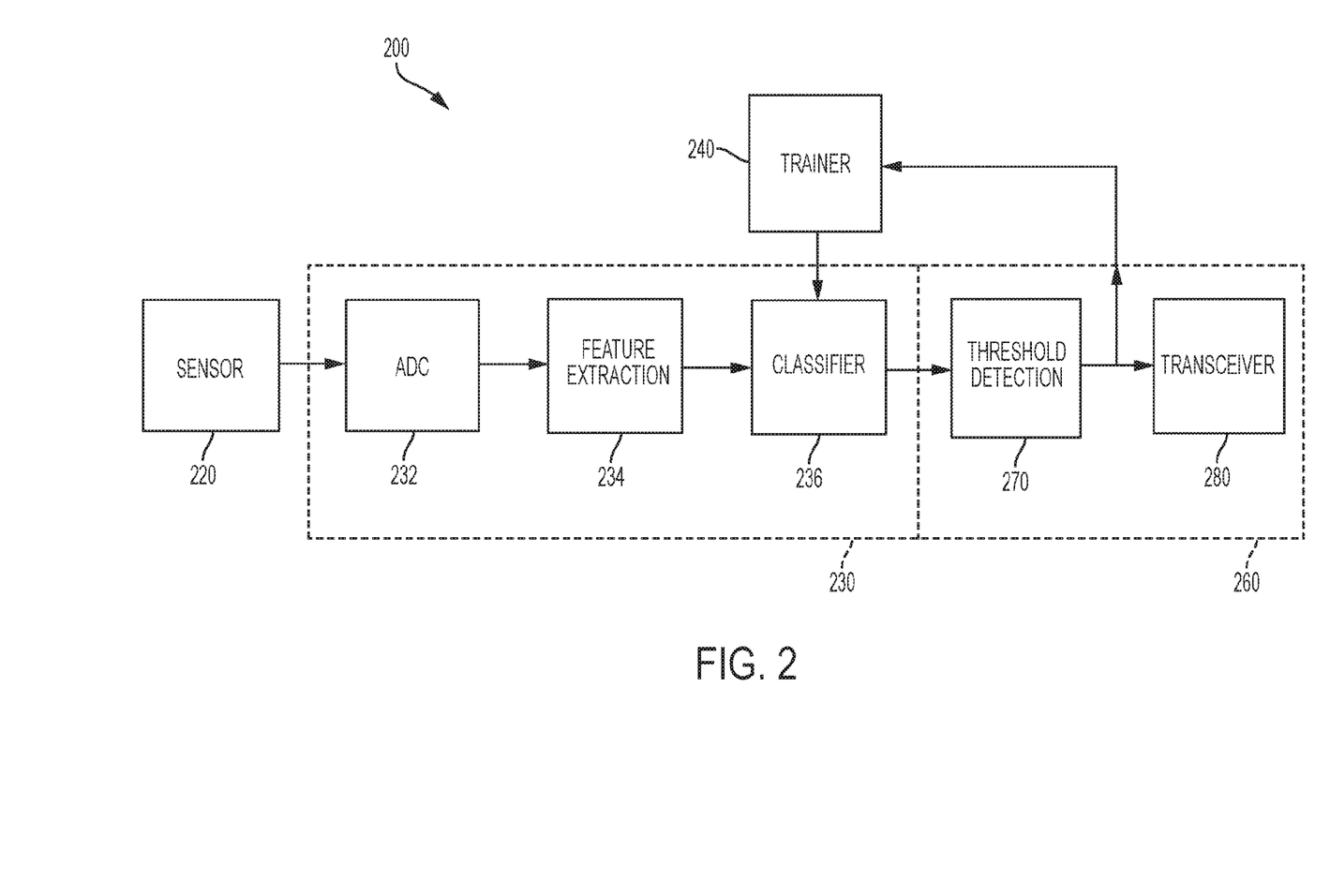
FIG. 2 depicts a block diagram of an exemplary sensor system according to one or more embodiments.

With reference to FIG. 2, a block diagram of an exemplary sensor system 200 of an embodiment is presented. Sensor system 200 includes a flexible substrate upon which are located one or more sensors 220 and a set of flexible transistors 230. Each of the flexible transistors 230 can have a construction similar to that of transistor 100. Sensor system 200 also includes a set of traditional transistors 260. In some embodiments, transistor set 230 can be of a construction similar to transistor 100.

Because transistor set 230 is located on the same flexible substrate, problems related to transmitting data, receiving data, and power consumption are significantly reduced. Transistor set 230 can perform a variety of tasks. In some embodiments, transistor set 230 can be optimized to perform certain tasks such as analog to digital conversion (represented by block 232), feature extraction (represented by block 234), and classifying (represented by block 236). Analog to digital conversion is the process of converting an analog signal into digital signal. Such conversions are common and known in the art.

Feature extraction is the process of taking the digital data and extracting the pertinent data. In the example given above, raw analog data from the heart can include all minor signals being detected by the sensor as well as the actual heartbeat, is analyzed to determine when the heart beat happens and, in some embodiments, the rate of the heartbeat. Similar types of feature extraction can occur with other types of sensors. For example, an averaging of data can occur. For a pressure or temperature sensor, instead of determining the instantaneous pressure or temperature, the pressure or temperature can be averaged (or smoothed) over a period of time, using one of a variety of different techniques. This period of time can vary based on what the sensor is measuring. For certain applications, the period of time can be relatively small period of time (such as one second or even less). For other applications, the period of time can be longer (such as one minute, one hour, or even longer).

Classifying can be a determination if what is measured by the sensor meets a certain criteria. The criteria can be different depending on what is being sensed. In some embodiments, the classifier is used to indicate when a certain criteria is reached at a sensor. When the criteria is reached, various actions can be taken, including, but not limited to, the sounding or transmission of an alarm. This varies depending on the type of sensor and what is being monitored. For example, a temperature sensor on a human might be programmed to sound an alarm if the temperature is over 38 degrees Celsius. But a temperature sensor on a computer processor might only sound an alarm if the temperature is over 80 degrees Celsius. A heart rate monitor can be programmed to sound an alarm either if it is too high or if it is too low.

The training of the classifier is another feature of certain embodiments. As discussed above, a sensor can have a different alarm condition depending on the use of the sensor. A temperature sensor can be used in both on a human or on a computer processor. If the temperature fluctuation during the normal operation is the signal to be classified (i.e., abnormal fluctuation sends an alarm), the temperature patterns under known normal operations and known abnormal operations have to be used to train the classifier. In order to be used in each different use case, the classifier 236 can be programmed before beginning use. In some embodiments, the programming of classier 236 can be accomplished through the use of a trainer 240. Trainer 240 can be an external device that interfaces with sensor system 200. Trainer 240 can be a machine-learning or other type of artificial intelligence system that learns characteristics of an item being measured. Machine-learning explores the study and construction of algorithms that can learn and make predictions on data. By learning the characteristics of the measured item, the sensor can set more reliable alarms. Not just in macro increments (e.g., the difference between a computer processor and a human being) but in small increments (e.g., a heart rate of 60 might be abnormally low for one person but be normal for another person). Historical data from the sensor can be used for this machine learning process to improve performance as time goes on as a feedback loop.

Also coupled to transistor set 230 is a traditional transistor set 260. In some embodiments, traditional transistor set 260 can include a plurality of silicon-based complementary metal oxide semiconductor (CMOS) transistors. Other types of transistors also can be used. Typically, the plurality of transistors would be placed on a wafer and packaged as an integrated circuit. The transistors would be coupled in any one of many different manners (both currently known or manners developed in the future) to perform computing functions. Exemplary functions that can be performed by traditional transistor set 260 include threshold detection (represented by block 270) and transceiver functions (represented by block 280). Threshold detection block 270 can be used in conjunction with trainer 240 to supplement the machine-learning of classifier 236. For example, threshold detection block 270 can be used to set or change the conditions when classifier 236 sends an alarm condition, via trainer 240. Trainer 240 can be a part of traditional transistor set 260 or it can be separate.

Transceiver 280 can be configured to transmit and receive data. In some embodiments, transceiver 280 can be configured to transmit and receive data to a computer system 300. Computer system 300 can be configured to work in conjunction with trainer 240 in order to provide machine-learning capabilities of classifier 236.

Figure 3:
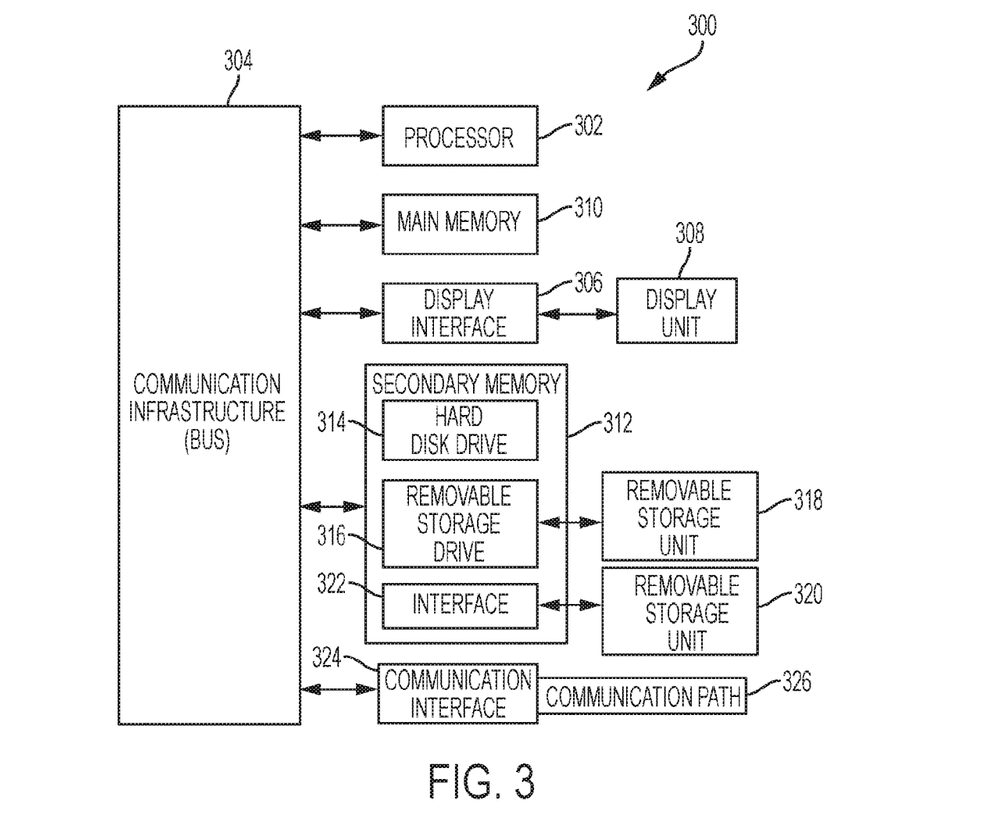
FIG. 3 depicts a computer system capable of implementing hardware components of one or more embodiments.

FIG. 3 depicts a high level block diagram computer system 300, which can be used to implement one or more embodiments. More specifically, computer system 300 can be used to implement hardware components of systems capable of performing methods described herein. Although one exemplary computer system 300 is shown, computer system 300 includes a communication path 326, which connects computer system 300 to additional systems (not depicted) and can include one or more wide area networks (WANs) and/or local area networks (LANs) such as the Internet, intranet(s), and/or wireless communication network(s). Computer system 300 and additional system are in communication via communication path 326, e.g., to communicate data between them. Computer system 300 can perform the tasks described above with respect to traditional transistor set 260.

Computer system 300 includes one or more processors, such as processor 302. Processor 302 is connected to a communication infrastructure 304 (e.g., a communications bus, cross-over bar, or network). Computer system 300 can include a display interface 306 that forwards graphics, textual content, and other data from communication infrastructure 304 (or from a frame buffer not shown) for display on a display unit 308. Computer system 300 also includes a main memory 310, preferably random access memory (RAM), and can also include a secondary memory 312. Secondary memory 312 can include, for example, a hard disk drive 314 and/or a removable storage drive 316, representing, for example, a floppy disk drive, a magnetic tape drive, or an optical disc drive. Hard disk drive 314 can be in the form of a solid state drive (SSD), a traditional magnetic disk drive, or a hybrid of the two. There also can be more than one hard disk drive 314 contained within secondary memory 312. Removable storage drive 316 reads from and/or writes to a removable storage unit 318 in a manner well known to those having ordinary skill in the art. Removable storage unit 318 represents, for example, a floppy disk, a compact disc, a magnetic tape, or an optical disc, etc. which is read by and written to by removable storage drive 316. As will be appreciated, removable storage unit 318 includes a computer-readable medium having stored therein computer software and/or data.

In alternative embodiments, secondary memory 312 can include other similar means for allowing computer programs or other instructions to be loaded into the computer system. Such means can include, for example, a removable storage unit 320 and an interface 322. Examples of such means can include a program package and package interface (such as that found in video game devices), a removable memory chip (such as an EPROM, secure digital card (SD card), compact flash card (CF card), universal serial bus (USB) memory, or PROM) and associated socket, and other removable storage units 320 and interfaces 322 which allow software and data to be transferred from the removable storage unit 320 to computer system 300.

Computer system 300 can also include a communications interface 324. Communications interface 324 allows software and data to be transferred between the computer system and external devices. Examples of communications interface 324 can include a modem, a network interface (such as an Ethernet card), a communications port, or a PC card slot and card, a universal serial bus port (USB), and the like. Software and data transferred via communications interface 324 are in the form of signals which can be, for example, electronic, electromagnetic, optical, or other signals capable of being received by communications interface 324. These signals are provided to communications interface 324 via communication path (i.e., channel) 326. Communication path 326 carries signals and can be implemented using wire or cable, fiber optics, a phone line, a cellular phone link, an RF link, and/or other communications channels.

In the present description, the terms "computer program medium," "computer usable medium," and "computer-readable medium" are used to generally refer to media such as main memory 310 and secondary memory 312, removable storage drive 316, and a hard disk installed in hard disk drive 314. Computer programs (also called computer control logic) are stored in main memory 310 and/or secondary memory 312. Computer programs can also be received via communications interface 324. Such computer programs, when run, enable the computer system to perform the features discussed herein. In particular, the computer programs, when run, enable processor 302 to perform the features of the computer system. Accordingly, such computer programs represent controllers of the computer system. Thus it can be seen from the forgoing detailed description that one or more embodiments provide technical benefits and advantages.

Figure 4:
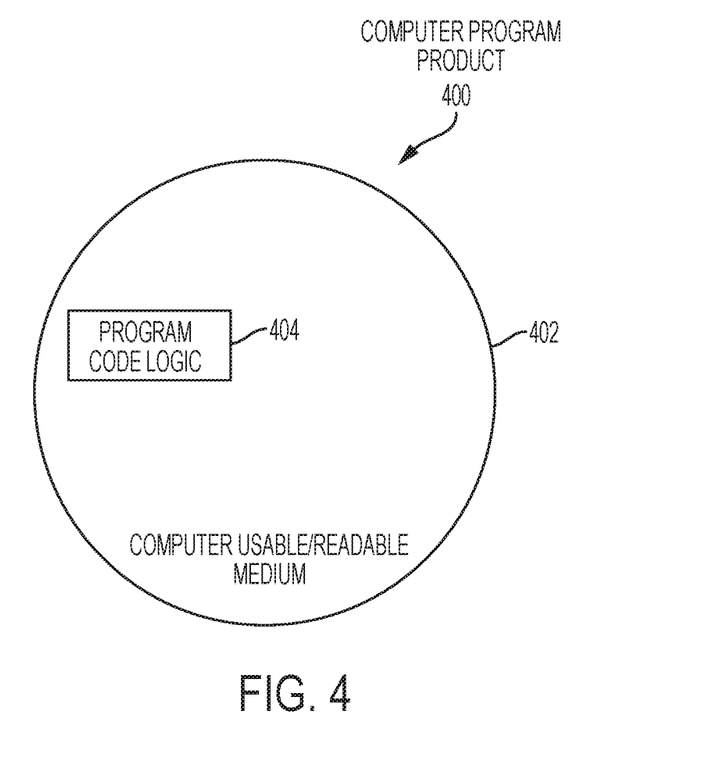
FIG. 4 depicts a diagram of a computer program product according to one or more embodiments.

Referring now to FIG. 4, a computer program product 400 in accordance with an embodiment that includes a computer-readable storage medium 402 and program instructions 404 is generally shown.

Embodiments may be a system, a method, and/or a computer program product. The computer program product may include a computer-readable storage medium (or media) having computer-readable program instructions thereon for causing a processor to carry out aspects of embodiments of the present invention.

The computer-readable storage medium can be a tangible device that can retain and store instructions for use by an instruction execution device. The computer-readable storage medium may be, but is not limited to, an electronic storage device, a magnetic storage device, an optical storage device, an electromagnetic storage device, a semiconductor storage device, or any suitable combination of the foregoing. A non-exhaustive list of more specific examples of the computer-readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer-readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer-readable program instructions described herein can be downloaded to respective computing/processing devices from a computer-readable storage medium or to an external computer or external storage device via a network, for example, the Internet, a local area network, a wide area network and/or a wireless network. The network may include copper transmission cables, optical transmission fibers, wireless transmission, routers, firewalls, switches, gateway computers, and/or edge servers. A network adapter card or network interface in each computing/processing device receives computer-readable program instructions from the network and forwards the computer-readable program instructions for storage in a computer-readable storage medium within the respective computing/processing device.

Computer-readable program instructions for carrying out embodiments may include assembler instructions, instruction-set-architecture (ISA) instructions, machine instructions, machine dependent instructions, microcode, firmware instructions, state-setting data, or either source code or object code written in any combination of one or more programming languages, including an object-oriented programming language such as Smalltalk, C++ or the like, and conventional procedural programming languages, such as the "C" programming language or similar programming languages. The computer-readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer-readable program instructions by utilizing state information of the computer-readable program instructions to personalize the electronic circuitry, in order to perform embodiments of the present invention.

Thus, it can be seen from the forgoing detailed description and accompanying illustrations that embodiments of the present invention provide structures and methodologies for providing sensors on flexible substrates that allow processing of sensor data via localized transistors that are also on the flexible substrates.

The descriptions of the various embodiments of the present invention have been presented for purposes of illustration, but are not intended to be exhaustive or limited to the embodiments described herein. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form described herein. Many modifications and variations will be apparent to those of ordinary skill in the art without departing from the scope and spirit of the invention. The embodiment was chosen and described in order to best explain the principles of the inventive teachings and the practical application, and to enable others of ordinary skill in the art to understand the invention for various embodiments with various modifications as are suited to the particular use contemplated.

The diagrams depicted herein are just one example. There can be many variations to this diagram or the operations described therein without departing from the spirit of the invention. For instance, the operations can be performed in a differing order or operations can be added, deleted or modified. All of these variations are considered a part of the claimed invention.

While various embodiments have been described, it will be understood that those skilled in the art, both now and in the future, can make various modifications which fall within the scope of the claims which follow. These claims should be construed to maintain the proper protection for the invention first described.

What is claimed is:

1. A system for sensing data comprising:
   one or more sensors formed on a substrate; and
   a plurality of transistors coupled to the one or more sensors and formed on the substrate;
   wherein a channel of each transistor of the plurality of transistors comprises a nanoscale material;
   wherein the plurality of transistors is configured to perform computing tasks including classifying data from the one or more sensors;
   wherein classifying data from the one or more sensors comprises using machine-learning techniques to classify data;
   wherein the system is further configured to perform threshold detection techniques using the classified data to determine if information should be transmitted;
   wherein the system is further configured to transmit threshold detection information after determining information should be transmitted; and
   wherein performing threshold detection techniques and transmitting threshold detection information occurs external to the substrate.

2. The system of claim 1, wherein each transistor of the plurality of transistors comprises:
   a gate on the substrate;
   a dielectric on the gate;
   a carbon-based nanostructure material over at least a portion of the dielectric, wherein at least a portion of the carbon-based nanostructure material serves as the channel of the transistor; and
   contacts coupled to one or more portions of the carbon-based nanostructure material on opposing sides of the channel, configured to serve as source and drain regions of the transistor.

3. The system of claim 2, wherein each transistor of the plurality of transistors further comprises an 3-Aminopropyl triethoxysilane (APTES) material configured to help deposition of the carbon-based nanostructure material.

4. The system of claim 2, wherein the gate comprises a first metal and a second metal.

5. The system of claim 2, wherein the dielectric comprises an aluminum oxide.

6. The system of claim 1, wherein the plurality of transistors is configured to perform computing tasks including analog-to-digital conversion of data from the one or more sensors.

7. The system of claim 1, wherein the plurality of transistors is configured to perform computing tasks including feature extraction of data from the one or more sensors, wherein feature extraction comprises processing data to determine important characteristics of the data.

8. The system of claim 1, wherein classifying data further comprises using historical data from the sensor to improve the machine-learning techniques.

9. The system of claim 1 wherein:
   the nanoscale material is chosen from one of the following: carbon nanotube, graphene, transition metal dichalcogenide materials, and phosphorene.

10. A method for sensing information comprising:
    sensing data using one or more sensors formed on a substrate;
    using a plurality of transistors coupled to the one or more sensors and formed on the substrate to performing computing tasks on the data;
    performing threshold detection techniques using the classified data to determine if information should be transmitted; and
    transmitting threshold detection information after determining information should be transmitted; wherein
    each transistor of the plurality of transistors comprises a nanoscale material;
    wherein the plurality of transistors is configured to perform computing tasks including classifying data from the one or more sensors;
    wherein classifying data from the one or more sensors comprises using machine-learning techniques to classify data; and wherein performing threshold detection techniques and transmitting threshold detection information occurs external to the substrate.

11. The method of claim 10 wherein:
each transistor of the plurality of transistors comprises:
  a gate on the substrate;
  a dielectric on the gate;
  a carbon-based nanostructure material over at least a portion of the dielectric, wherein at least a portion of the carbon-based nano structure material serves as a channel of the transistor; and
  contacts coupled to one or more portions of the carbon-based nanostructure material on opposing sides of the channel, configured to serve as source and drain regions of the transistor.

12. The method of claim 11 wherein:
performing computing tasks includes performing analog-to-digital conversion of the data from the one or more sensors.

13. The method of claim 11 wherein:
performing computing tasks includes performing feature extraction of data from the one or more sensors, wherein feature extraction comprises processing data to determine important characteristics of the data.

14. The method of claim 11 wherein:
classifying data further comprises using historical data from the sensor to improve the machine-learning techniques.

15. A computer-readable storage medium having program instructions embodied therewith, wherein the computer-readable storage medium is not a transitory signal per se, the program instructions readable by a processor system to cause the processor system to perform a method comprising:
  performing analog-to-digital conversion of data from one or more sensors;
  performing feature extraction of data from the one or more sensors, wherein feature extraction comprises processing data to determine important characteristics of the data;
  performing threshold detection techniques using the classified data to determine if information should be transmitted; and
  transmitting threshold detection information after determining information should be transmitted;
  perform computing tasks including classifying data from the one or more sensors;
  wherein classifying data from the one or more sensors comprises using machine-learning techniques to classify data;
  wherein classifying data further comprises using historical data from the sensor to improve the machine-learning techniques; and wherein
  the processor system comprises a plurality of transistor formed on a substrate;
  the processor system is coupled to one or more sensors that are formed on the substrate; and
  wherein a channel of each transistor of the plurality of transistors comprises a carbon nanoscale material;
  wherein the plurality of transistors is configured to perform computing tasks including classifying data from the one or more sensors;
  wherein classifying data from the one or more sensors comprises using machine-learning techniques to classify data; and
  wherein performing threshold detection techniques and transmitting threshold detection information occurs external to the substrate.

\* \* \* \* \*